United States Patent [19]

Treace

[11] 4,131,956
[45] Jan. 2, 1979

[54] ELBOW PROSTHESIS

[75] Inventor: James T. Treace, Malibu, Calif.

[73] Assignee: Richards Manufacturing Company, Inc., Memphis, Tenn.

[21] Appl. No.: 768,605

[22] Filed: Feb. 14, 1977

[51] Int. Cl.² .............................................. A61F 1/24
[52] U.S. Cl. ...................................... 3/1.91; 128/92 C
[58] Field of Search .................................. 3/1.9–1.913; 128/92 C, 92 CA

[56] References Cited

U.S. PATENT DOCUMENTS

| | | | |
|---|---|---|---|
| 3,798,679 | 3/1974 | Ewald | 3/1.91 X |
| 3,816,854 | 6/1974 | Schlein | 3/1.91 |
| 3,837,009 | 9/1974 | Walker | 3/1.911 |
| 3,852,831 | 10/1974 | Dee | 3/1.91 |
| 3,868,730 | 3/1975 | Kaufer et al. | 3/1.91 |
| 3,919,725 | 11/1975 | Swanson et al. | 3/1.91 |
| 3,990,117 | 11/1976 | Pritchard et al. | 3/1.91 |
| 4,057,858 | 11/1977 | Helfet | 3/1.91 |

FOREIGN PATENT DOCUMENTS

| | | | |
|---|---|---|---|
| 1902700 | 8/1970 | Fed. Rep. of Germany | 3/1.91 |
| 1099519 | 3/1955 | France | 3/1.913 |
| 1122634 | 5/1956 | France | 128/92 C |
| 471394 | 5/1952 | Italy | 3/1.913 |

Primary Examiner—Ronald L. Frinks

[57] ABSTRACT

An elbow prosthesis for replacing one or more of the articulating surfaces of the elbow joint in a human elbow. An ulna component for being fixedly anchored to the proximal end of the ulna of a human elbow joint is provided with a head member having a curved face portion for replacing the articulating surface of the proximal end of the ulna. A humeral component for being fixedly anchored to the distal end of the humerus of a human elbow joint is provided with a head member having a curved face portion for replacing the articulating surface of the distal end of the humerus.

4 Claims, 8 Drawing Figures

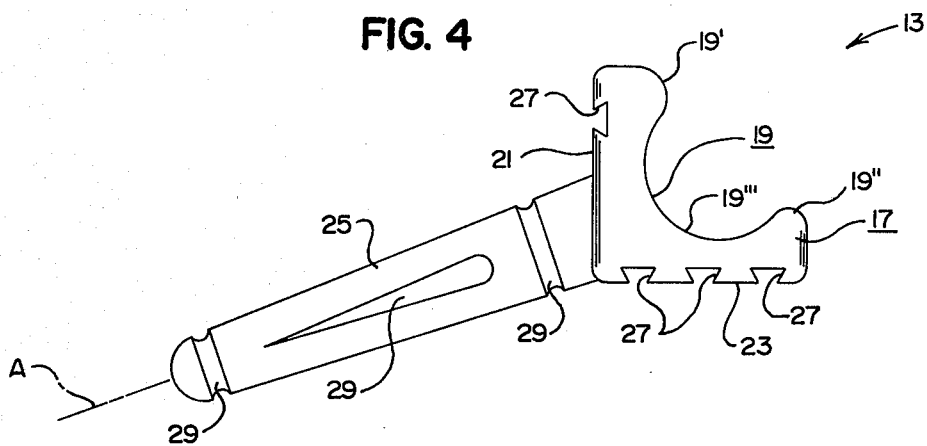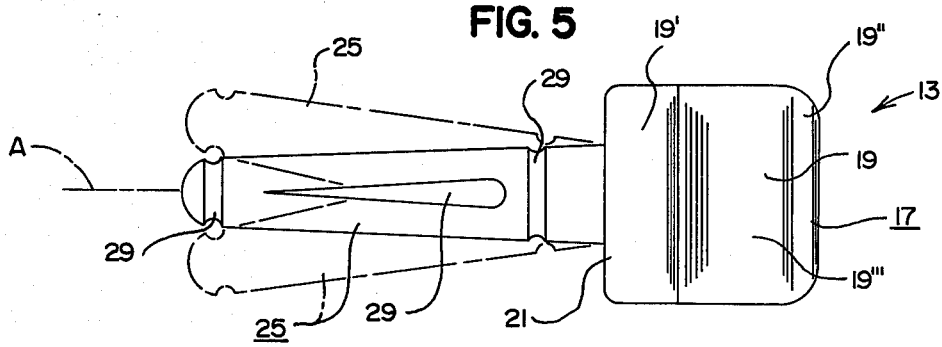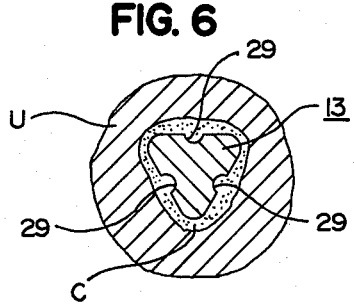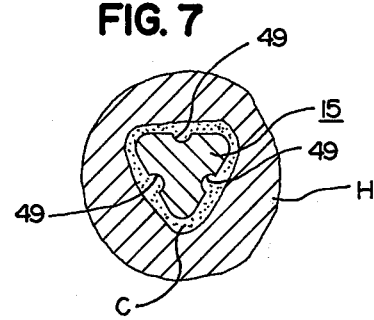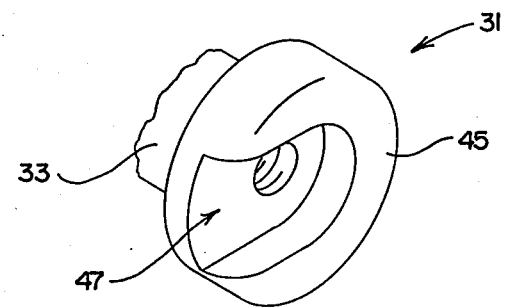

ELBOW PROSTHESIS

BACKGROUND OF THE INVENTION

1. Field of the Invention

This invention relates to the field of prostheses for the human elbow.

2. Description of the Prior Art

Heretofore, correction of the diseased or otherwise defective articulating surfaces of a human elbow joint has taken three basic forms: (1) fusion of the elbow joint, (2) replacement of the elbow joint with a hinged-type prosthesis, or (3) arthoroplasty (i.e., the mere removal of the diseased or otherwise defective portion of the elbow joint). All of these forms are disadvantageous for one reason or another. For example, fusion of the elbow joint is obviously disadvantageous since it prevents any flexion of the elbow. Hinged type prostheses are also disadvantageous since they do not allow normal full range motion of the elbow joint without putting stress on the bone and/or implants which results in, for example, early failure of such implants. Arthroplasty results in a weak, fragile elbow joint.

The inventor is aware of the following U.S. patents which relate generally to the present invention: Averill et al, U.S. Pat. Nos. 3,728,742 and Kaufer et al, 3,868,730. Both of these patents disclose prostheses designed primarily for replacing the articulating surfaces of a human knee joint. The Averill et al. patent discloses a joint prosthesis consisting of an upper member and a lower member with the upper member having a pair of spaced condyle portions joined together by an intercondyloidal segment and with the lower member having a pair of similarly spaced plateau portions joined by an interplateau segment for receiving the condyle portions of the upper member. The Kaufer et al patent discloses a hinged-type prosthesis consisting of a femoral and a tibial component rotatably coupled together by a ball and socket connection. Neither of the above patents disclose or suggest the present invention.

SUMMARY OF THE INVENTION

The present invention is directed towards overcoming problems and disadvantages of prior ways of correcting diseased or otherwise defective articulating surfaces of a human elbow joint. The concept of the present invention is to provide elbow prostheses for replacing one or more of the articulating surfaces of the elbow joint in a human elbow. The elbow prosthesis of the present invention includes, in general, an ulna component means for being fixedly anchored to the proximal end of the ulna of a human elbow joint, the ulna component means including a single head member having a curved face portion for replacing the articulating surface of the proximal end of the ulna; and/or a humeral component means for being fixedly anchored to the distal end of the humerus of a human elbow joint, the humeral component means including a single head member having a curved face portion for replacing the articulating surface of the distal end of the humerus and for articulatingly coacting with the articulating surface of the proximal end of the ulna or with the curved face portion of the ulna component means.

BRIEF DESCRIPTION OF THE DRAWINGS

FIG. 4 is a side elevational view of the ulna component of the elbow prosthesis of the present invention.

FIG. 5 is a top plan view of the ulna component means of the elbow prosthesis of the present invention showing modified embodiments thereof in broken lines.

FIG. 6 is a sectional view of the ulna component means of the elbow prosthesis of the present invention as taken on line VI—VI of FIG. 1.

FIG. 7 is a sectional view of the humeral component means of the elbow prosthesis of the present invention as taken on line VII—VII of FIG. 1.

FIG. 8 is a perspective view of a portion of the humeral component means of the elbow prosthesis of the present invention.

DESCRIPTION OF THE PREFERRED EMBODIMENT

The elbow prosthesis 11 of the present invention (see, in general, FIG. 1) is for being implanted in a human elbow to replace one or more of the articulating surfaces of the human elbow joint. The elbow prosthesis 11 may include an ulna component means 13 for being fixedly anchored to the proximal end U' of the ulna U of a human elbow joint to replace the articulating surface thereof (see, in general, FIG. 1). The elbow prosthesis 11 may also include a humeral component means 15 for being fixedly anchored to the distal end H' of the humerus H of a human elbow joint to replace the articulating surface thereof (see, in general, FIG. 1).

Figure 1:
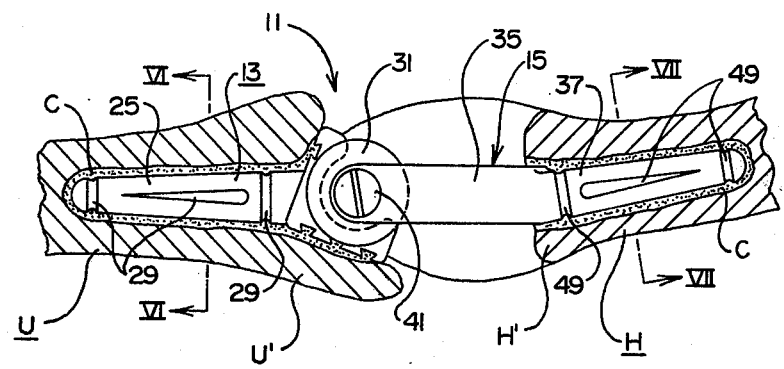
FIG. 1 is a side elevational view of the elbow prosthesis of the present invention shown implanted in a human elbow joint.

The ulna component means 13 (see, in general, FIGS. 4 and 5) includes a single head member 17 having a curved face portion 19 for replacing the articulating surface of the proximal end U' of the ulna U (i.e., the end opposite the hand). The curved face portion 19 includes protruding ridge-like rounded portions 19', 19" extending transversely and an intermediate recessed portion 19''' curved in the shape of a portion of an imaginary cylinder with its axis extending transversely. In other words, recess portion 19''' is curved in the shape of a portion of a cylinder (i.e., substantially one-half of a cylinder) to establish a recess and with the edges of head member 17 being reversely curved from that of portion 19''' to establish the protruding portions 19', 19". Thus, the curvature of the curved face portion 19 is preferably the same as that of a healthy articulating surface of the proximal end of an ulna for allowing the ulna component means 13 to articulatingly coact with the articulating surface of the distal end H' of the humerus H of the human elbow (i.e., the end opposite the shoulder) or with the humeral component means 15 and so as to provide a totally unconstrained, substantially loose joint between the ulna U and the humerus H. The head member 17 is preferably substantially L-shaped (see FIGS. 1 and 4) and preferably includes a substantially flat backside 21 and a substantially flat underside 23 for engaging the proximal end U' of the ulna U as shown in FIG. 1. The backside 21 and underside 23 of the head member 17 are preferably joined together at one end to form the substantially L-shape of the head member 17. The backside 21 and the underside 23 being arranged at substantially 90° relative to one another and being flat are so shaped to ease the surgical preparation of the bone so that an accurate fit of the ulna component means 13 is possible without the necessity of extensive alignment templates and alignment jigs. The ulna component means 13 also preferably includes a substantially spikelike body member 25 fixedly attached to the backside 21 of the head member 17 of the ulna component means 13 for extending into the proximal end U' of the ulna U. The backside 21 and underside 23 of the head member 17 of the ulna component means 13 preferably has a plurality of transverse grooves 27 provided therein for coacting with bone cement C or the like to fixedly anchor the ulna component means 13 to the proximal end U' of the ulna C (see FIG. 1). The transverse grooves 27 are preferably undercut to form dovetail-like grooves as clearly shown in FIGS. 1 and 4. The spike-like body member 25 of the ulna component means 13 likewise preferably has a plurality of transverse and longitudinal grooves 29 therein for coacting with bone cement C or the like to fixedly anchor the ulna component means 13 to the proximal end U' of the ulna U (see FIGS. 1 and 6). It should be noted that the transverse grooves 29 in the spike-like body member 25 are preferably in the form of concentric rings about the spike-like body member 25 as apparent from FIGS. 1, 4 and 5. The spike-like body member 25 of the ulna component means 13 is preferably substantially triangular in cross-section (see FIG. 6) for preventing rotation of the ulna component means 13 in the proximal end U' of the ulna U. The spike-like body member 25 preferably tapers inwardly towards the end thereof opposite the head member 17 to form a pyramid-like structure having a substantially rounded outer end as shown in FIGS. 1, 4 and 5. The longitudinal axis A of the spike-like body member 25 of the ulna component means 13 is preferably positioned at an optimum angle relative to the backside 21 of the head member 17 of the ulna component means 13, so as to duplicate the normal carrying angle of the human elbow. More specifically, the longitudinal axis A of the spike-like body member 25 preferably angles downwardly from the backside 21 of the head member 17 at an angle of substantially 20 degrees from the perpendicular as shown in FIG. 4, so as to duplicate the normal angle relationship of the face of a healthy ulna articular surface to that of its corresponding (ulna) intermedullary shaft (d). In addition, the longitudinal axis A of the spike-like body member 25 may be angled sideward from the backside 21 of the head member 17 at an angle of substantially 10 degrees to either the right or left, as shown in broken lines in FIG. 5, depending on whether the ulna component means 13 is intended for use with a right or left arm elbow joint. The sideward angle of the longitudinal axis A of the spike-like body member 25 may be neutral as shown in solid lines in FIG. 5 for those cases where the carrying angle of the arm has been destroyed by disease or the like.

Figure 2:
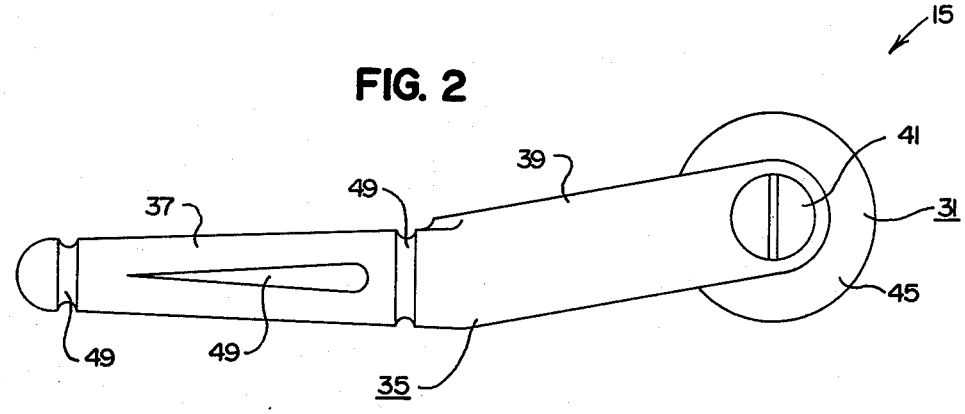
FIG. 2 is a side elevational view of the humeral component of the elbow prosthesis of the present invention.
Figure 3:
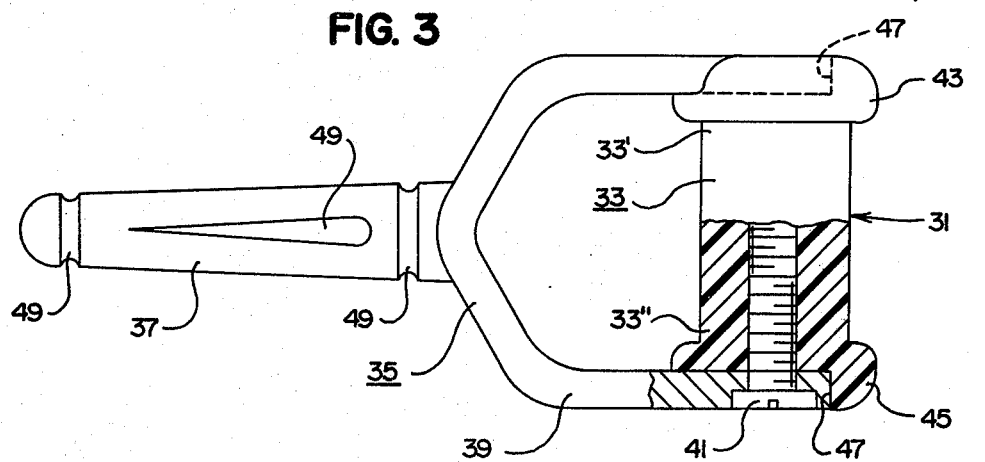
FIG. 3 is a partially sectional top plan view of the humeral component of the elbow prosthesis of the present invention.

The humeral component means 14 (see, in general, FIGS. 2 and 3) of the elbow prosthesis 11 includes a single head member 31 having a curved face portion for replacing the articulating surface of the distal end H' of the humerus H (i.e., the end opposite the shoulder) to articulatingly coact with the articulating surface of the proximal end U' of the ulna U or with the ulna component means 13. The curved face portion of the head member 31 of the humeral component means 15 preferably has substantially the same curvature as that of a healthy articulating surface of the distal end of a humerus for articulatingly coacting with the articulating surface of the proximal end U' of the ulna U or with the curved face portion 19 of the ulna component means 13 in the same manner as a healthy articulating surface of the distal end of a humerus articulatingly coacts with the healthy articulating surface of the proximal end of an ulna and so as to provide a totally unconstrained, substantially loose joint between the ulna U and the humerus H, simulating the function of the normal elbow joint. The head member 31 of the humeral component means 15 preferably includes an elongated, substantially cylindrical portion 33 (see, in general, FIG. 3) for forming the curved face portion thereof and for replacing the articulating surface of the distal end H' of the humerus H. The cylindrical portion 33 includes a first end 33' and a second end 33". The humeral component means 15 preferably includes a substantially Y-shaped body member 35 (see, in general, FIG. 3) for being fixedly anchored to the distal end H' of the humerus H. The body member 35 preferably includes a substantially spike-like first end 37 for extending into the distal end H' of the humerus and preferably includes a substantially U-shaped second end 39 fixedly attached to the spike-like first end 37. The cylindrical portion 33 of the head member 31 preferably extends across the mouth of the U-shaped second end 39 of the body member 35 of the humeral component means 15 as shown in FIG. 3. Screws 41 or the like are used to fixedly attach the cylindrical portion 33 to the U-shaped second end 39 of the body member 35 (see, in general, FIG. 3). The head member 31 of the humeral component means 15 preferably includes a first flange portion 43 fixedly attached to the first end 31' of the cylindrical portion 33 thereof and preferably includes a second flange portion 45 fixedly attached to the second end 33" of the cylindrical portion 33 thereof causing said head member 31 to resemble a barbell for restricting lateral movement of the humeral component means 15 when the humeral component means 15 is fixedly anchored to the distal end H' of the humerus H and is articulatingly engaged in the articulating surface of the proximal end U' of the ulna U or the ulna component means 13 as will be apparent to those skilled in the art. Thus, the width of head member 31 between flange portions 43, 45 is just slightly greater than the width of head member 17 so that lateral movement of ulna component means 13 is restricted relative to humeral component means 15 to provide medial-lateral stability of elbow prosthesis 11. The head member 33 is preferably non-rotatably mounted to the U-shaped second end 39 of the body member 35 in any manner apparent to those skilled in the art. For example, a groove 47 may be provided in the outer side of each flange portion 43, 45 as clearly shown in FIGS. 3 and 8 for allowing each leg of the U-shaped second end 39 of the body member 35 to extend therein and to thereby prevent the head member 31 from rotating relative to the body member 35 as will be apparent to those skilled in the art. The spike-like first end 37 of the body member 35 of the humeral component means 15 preferably has a plurality of transverse and longitudinal grooves 49 therein for coacting with bone cement C to fixedly anchor the humeral component means 15 to the distal end H' of the humerus H (see, in general, FIGS. 1 and 7). It should be noted that the transverse grooves 49 in the spike-like first end 37 may preferably be in the form of concentric rings about the spike-like first end 37 as apparent from FIGS. 1, 2 and 3. The spike-like first end 37 of the body member 35 of the humeral component means 15 preferably is substantially triangular in cross-section as shown in FIG. 7 for preventing rotation of the humeral component means 15 in the distal end H' of the humerus H. The spike-like first end 37 preferably tapers inwardly towards the end thereof opposite the U-shaped second end 39 to form a pyramid-like structure having a substantially rounded outer end as shown in FIGS. 1, 2 and 3.

The head member 31 of the humeral component means 15 is preferably constructed of a biocompatible plastic (e.g., ultra-high molecular weight polyethylene) for reducing friction and for acting as a shock absorber between the humeral component means 15 and the articulating surface of the distal end of an ulna or the ulna component means 13. The ulna component means 13 and the body member 35 of the humeral component means 15 are preferably constructed of a biocompatible metal. All corners of the head member 31 are preferably rounded to ease insertion and to prevent tissue irritation that would be created by straight or sharp edges.

To implant the elbow prosthesis 11 in a human elbow, first a posterior long incision is preferably made. This incision gives the option of osteotomizing the olecranon or simply reflecting the triceps tendon attachment to the olecranon as will be apparent to those skilled in the art. The incision starts about 3 inches distal to the tip of the olecranon process and then extends upward for the desired distance, while being centered over the dorsal margin of this process and the triceps tendon. The skin and deep fascia are undercut as far as the medial and lateral epicondyles of the humerus. The ulnar nerve is located along the medial margin of the triceps muscle, posterior to the medial intermuscular septum. Placing a hernia tape round the nerve will facilitate its careful handling. The nerve then is dissected free from the surrounding tissues for the entire length of the wound. The olecranon process distal to the triceps insertion is exposed subperiosteally. The olecranon is osteotomized 1 inch distal to its tip, and the proximal fragment is lifted upward to expose the interior of the joint. The next incision is made along the lateral margin of the triceps tendon, up to the lateral epicondyle. The tendon is thus separated from the anconeous muscle radially, and then the capsule and synovia are opened. A similar incision is made along the medial margin of the triceps tendon, up to the medial epicondyle, followed by the cutting of the capsule and synovia of this portion of the joint. The interior of the elbow joint is thus made completely accessible. The posterior surface of the distal fourth of the humerus H can be exposed to view similarly by raising the triceps muscle subperiosteally and retracting it upward. On closing the wound, it is of the utmost importance that the olecranon process be restored accurately and that the ulnar nerve be transplanted anteriorly to the elbow. If the osteotomized portion of the olecranon is small, it may be excised and the triceps reattached to the proximal end of the remaining part of the process. If the radial head is present and diseased, osteotomy should be accomplished at this time at the normal level of radial head ostectomy. If the radial head appears unaffected, at the surgeon's discretion, it may be left intact. Using a power saw (osteotome can cause splitting) vertical and horizontal cuts are made to "square up" the articular surface of the ulna U. A trial ulna component (left, right or neutral) is preferably used to determine these cuts. The medullary shaft of the ulna U is identified and sized using an ulna broach. Trial fitting should continue until level placement of the trial component is maintained. Care should be taken at this point not to osteotomize too great an amount or at too great an angle off the medial portion of the ulna U.

Using a humeral trial as a template, the general outline thereof is preferably laid out of the humerus H. The stem of the humeral trial should be in line with the humeral shaft. Using a ¼ inch or 3/16 inch twist drill, the humeral medullary shaft is established by penetrating through the approximate center of the humeral condyle articular surface and continue through to the medullary canal. A broach may be used to enlarge this hole. The trial humeral component stem may be inserted into this hole and a more accurate approximation of remaining bone to be removed judged. A power saw is then used to remove the center portion of the distal humeral condyle preserving the lateral and medial epicondyles. Final trial fitting will be complete when the trial humeral component will seat loosely and with the curved face portion thereof flush with the surface of the distal humeral epicondyles. With both trial components in place the joint motion is checked and any blocks thereof are identified. Full extension should be demonstrated. If the components tend to "rock apart" impingements may be present. Excess bone on the radial head, medial ulna neck, and lateral or medial humeral epicondyles is checked for. Usually excess radial head is present and prevents full flexion. If the triceps tendon attachment was reflected it is suggested that prior to the final cementing procedure, 7/64 inch drill holes be placed through the olecranon and non-absorbable sutures placed therein and held clear. After cementing of the components, the triceps tendon can be reattached to the olecranon bed by these sutures. The proper final components are then readied. From previous experience it has been found that both components are best cemented into place at the same time, utilizing one unit of cement. The ulna component means 13 is placed in first, excess cement removed, then the humeral component means 15 is inserted with removal of additional excess cement. The joint is then reduced and carried through a range of motion while the cement is still soft. Excess cement is then removed and the joint held in full extension until cement has hardened. The osteotomized portion of the olecranon is then reattached (if present) or the triceps tendon is reattached using the previously placing sutures. Closed suction drains are suggested and the wound is preferably closed in layers. Soft bulky dressing is recommended and removal of the closed suction drains within 18 hours. Active motion within tolerance is suggested on the second to third day. Stitches are preferably removed on the tenth day with continued motion and gentle physical therapy encouraged to maintain range of motion after wound healing. Passive motion should be avoided but required if improvement is not noted. Manipulation is at surgeon's discretion.

As thus constructed and used, the present invention provides an elbow prosthesis which can be used as an alternaive to fusion or hinged-type implants for patients with ligamentous statality and with intact medial and lateral humeral epicondyles, which requires a minimum of bone removal for implantation due to the non-hinged design, which is easily inserted, which does not put stress on the bones or implants as does hinged-type implants since the forces that would normally cause a hinged-type implant to loosen or fatigue will simply cause the elbow prosthesis 11 to spring apart simulating the function of the normal elbow joint, and which provides a totally unconstrained, substantially loose joint between the ulna and the humerus of a human elbow joint.

Although the invention has been described and illustrated with respect to a preferred embodiment thereof, it is not to be so limited since changes and modifications may be made therein which are within the full intended scope of the invention.

I claim:

1. An elbow prosthesis for implanting in a human elbow, said elbow prosthesis comprising: a humeral component means for being fixedly anchored to the distal end of the humerus in a human elbow to replace the articulating surface thereof, said humeral component means including a single head member having a curved face portion for replacing the articulating surface of the distal end of the humerus, said humeral component means including a substantially Y-shaped body member for being fixedly anchored to the distal end of the humerus, said head member of humeral component means including an elongated, substantially cylindrical portion fixedly attached to said body member of said humeral component means for replacing the articulating surface of the distal end of the humerus to articulatingly coact with the articulating surface of the proximal end of the ulna of the human elbow, said cylindrical portions extending across the mouth of said Y-shaped body member of said humeral component means, said head member of said numeral component means including a first flange portion fixedly attached to said first end of said cylindrical portion thereof and including a second flange portion fixedly attached to said second end of said cylindrical portion thereof for restricting lateral movement of said humeral component means when said humeral component means is fixedly anchored to the distal end of the humerus and is articulatingly engaging the articulating surface of the proximal end of the ulna.

2. The elbow prosthesis of claim 1 in which said cylindrical portion of said humeral component means is constructed of plastic for reducing friction and acting as a shock absorber between said humeral component means and the articulating surface of the proximal end of the ulna.

3. An elbow prosthesis for implanting with cement in a human elbow, said elbow prosthesis comprising:

(a) an ulna component means for being fixedly anchored to the proximal end of the ulna of a human elbow joint to replace the articulating surface thereof, said ulna component means including a single head member having a curved face portion for replacing the articulating surface of the proximal end of the ulna, said head member being substantially L-shaped and having a substantially flat backside and a substantially flat underside for engaging the proximal end of the ulna, said backside and said underside being joined together at one end to form said substantially L-shape, said backside and said underside of said head member of said ulna component means have a plurality of transverse grooves therein for coacting with bone cement to fixedly anchor said ulna component means to the proximal end of the ulna, said ulna component means including a spike-like body member fixedly attached to said backside of said head member for extending into the proximal end of the ulna, said spike-like body member of said ulna component means has a plurality of transverse and longitudinal grooves therein for coacting with bone cement to fixedly anchor said ulna component means to the proximal end of the ulna, said spike-like body member being substantially triangular in cross-section for preventing rotation of said ulna component means in the proximal end of the ulna and having smoothly rounded edges; and (b) a humeral component means for being fixedly anchored to the distal end of the humerus of a human elbow joint to replace the articulating surface thereof, said humeral component means including a single head member having a curved face portion for replacing the articulating surface of the distal end of the humerus and for articulatingly coacting with said curved face portion of said ulna component means, said humeral component means including a substantially Y-shaped body member for being fixedly anchored to the distal end of the humerus, said Y-shaped body member of said humeral component means including a substantially spike-like first end for extending into the distal end of the humerus and including a substantially U-shaped second and fixedly attached to said spike-like first end, said head member of said humeral component means including an elongated, substantially cylindrical portion fixedly attached to said body member of said humeral component for replacing the articulating surface of the distal end of the humerus to articulatingly coact with said curved face-portion of said head member of said ulna component means, said cylindrical portion extending across the mouth of said U-shaped end of said body member of said humeral component means, said cylindrical portion of said head member of said numeral component means including first and second ends, said head member of said humeral component means including a first flange member fixedly attached to said first end of said cylindrical portion thereof and including a second flange portion fixedly attached to said second end of said cylindrical portion thereof for restricting lateral movement of said humeral component means when said humeral component means is fixedly anchored to the distal end of the humerus and is articulatingly engaging said ulna component means, said spike-like first end of said body member of said humeral component means being substantially triangular in cross-section for preventing rotation of said humeral component means in the distal end of the humerous and having smoothly rounded edges, said spike-like first end of said body member of said humeral component means has a plurality of transverse and longitudinal grooves therein for coacting with bone cement to fixedly anchor said humeral component means to the distal end of the humerus.

4. The elbow prosthesis of claim 3 in which said head member of said humeral component means is constructed of plastic for reducing friction and acting as a shock absorber between said humeral component means and said ulna component means; and in which said ulna component means and said body member of said humeral component means are constructed of a biocompatible metal.

* * * * *